(12) United States Patent
Bor et al.

(10) Patent No.: US 10,568,764 B2
(45) Date of Patent: Feb. 25, 2020

(54) SYSTEM AND METHODS FOR DEPTH DETECTION IN LASER-ASSISTED OPHTHALMIC PROCEDURES

(71) Applicant: AMO DEVELOPMENT, LLC., Santa Ana, CA (US)

(72) Inventors: Zsolt Bor, San Clemente, CA (US); Peter-Patrick De Guzman, Orange, CA (US); Anthony Dennison, Irvine, CA (US); Michael Campos, Round Rock, TX (US)

(73) Assignee: AMO Development, LLC, Santa Ana, CA (US)

( * ) Notice: Subject to any disclaimer, the term of this patent is extended or adjusted under 35 U.S.C. 154(b) by 727 days.

(21) Appl. No.: 13/830,072

(22) Filed: Mar. 14, 2013

(65) Prior Publication Data

US 2014/0276679 A1    Sep. 18, 2014

(51) Int. Cl.
*A61F 9/008* (2006.01)

(52) U.S. Cl.
CPC .................................. *A61F 9/0084* (2013.01)

(58) Field of Classification Search
CPC .................... A61F 9/0084; A61F 9/008; A61F 2009/00878; A61B 18/203
USPC ......................................................... 606/2–19
See application file for complete search history.

(56) References Cited

U.S. PATENT DOCUMENTS

| 4,665,913 A | 5/1987 | L'esperance, Jr. |
| 4,669,466 A | 6/1987 | L'esperance |
| 4,732,148 A | 3/1988 | L'esperance, Jr. |
| 4,764,930 A | 8/1988 | Bille et al. |
| 4,770,172 A | 9/1988 | L'esperance, Jr. |
| 4,773,414 A | 9/1988 | L'esperance, Jr. |

(Continued)

FOREIGN PATENT DOCUMENTS

| WO | WO-2010022754 A1 | 3/2010 | |
| WO | WO 2012178054 A1 * | 12/2012 | ............... A61B 3/10 |
| WO | WO-2012178054 A1 | 12/2012 | |

OTHER PUBLICATIONS

Semrock, High-reflectivity Mirrors, http://www.semrock.com/high-reflectivity-mirrors.aspx.*

(Continued)

*Primary Examiner* — Carl H Layno
*Assistant Examiner* — Dacheng Xie
(74) *Attorney, Agent, or Firm* — Johnson & Johnson Surgical Vision, Inc.

(57) ABSTRACT

Embodiments of this invention relate to systems and methods for automatic depth (or Z) detection before, during, or after laser-assisted ophthalmic surgery. When performing ophthalmic laser surgery, the operator (or surgeon) needs to make accurate and precise incisions using the laser beam. With the automatic depth detection systems and methods, the same laser used for the surgical procedure may be used for depth measurement of the surgical incisions. The surgical laser system may include a laser delivery system for delivering a pulsed laser beam to photoalter an eye, a mirror to transmit at least a portion of reflected light of the pulsed laser beam, a lens positioned to focus the transmitted reflected lighted on to a detector, (such as a CCD), and a depth encoder configured to automatically detect depth according to one or more of color, intensity, or shape of the focused spot on the CCD.

8 Claims, 4 Drawing Sheets

(56) References Cited

U.S. PATENT DOCUMENTS

| | | | |
|---|---|---|---|
| 5,108,388 A | | 4/1992 | Trokel et al. |
| 5,162,641 A | * | 11/1992 | Fountain .................... 250/201.2 |
| 5,163,934 A | | 11/1992 | Munnerlyn |
| 5,207,668 A | | 5/1993 | L'esperance, Jr. |
| 5,219,343 A | | 6/1993 | L'esperance, Jr. |
| 5,646,791 A | | 7/1997 | Glockler |
| 5,993,438 A | | 11/1999 | Juhasz et al. |
| D462,442 S | | 9/2002 | Webb |
| 6,623,476 B2 | | 9/2003 | Juhasz et al. |
| 6,863,667 B2 | | 3/2005 | Webb et al. |
| 7,351,241 B2 | | 4/2008 | Bendett et al. |
| 7,887,184 B2 | | 2/2011 | Baer et al. |
| 2009/0131921 A1 | * | 5/2009 | Kurtz et al. ....................... 606/4 |
| 2009/0137988 A1 | * | 5/2009 | Kurtz ...................... A61F 9/008 606/4 |
| 2010/0004641 A1 | * | 1/2010 | Frey ........................ A61F 9/008 606/4 |
| 2010/0130966 A1 | * | 5/2010 | Brownell ................ A61F 9/008 606/4 |
| 2010/0324543 A1 | * | 12/2010 | Kurtz ...................... A61F 9/008 606/6 |
| 2012/0016349 A1 | * | 1/2012 | Brownell ......................... 606/4 |

OTHER PUBLICATIONS

Edmund Optics, Lens Laser Grade PCX 25mm DIAM x 100mm FL 1064 nm, prnt_67976.pdf.*

Olympus Microscopy Resource Center, Anatomy of a Charge-Coupled Device, http://www.olympusmicro.com/primer/digitalimaging/concepts/ccdanatomy.html.*

Gray Institute, A 4-quadrant photodiode detector system, A 4-quadrant Photodiode detector system.pdf.*

International Search Report and Written Opinion for Application No. PCT/US2014/018624, dated May 2, 2014, 12 pages.

* cited by examiner

SYSTEM AND METHODS FOR DEPTH DETECTION IN LASER-ASSISTED OPHTHALMIC PROCEDURES

TECHNICAL FIELD

Embodiments of the present invention generally relate to laser-assisted ophthalmic procedures, and more particularly, to systems and methods for depth detection during laser-assisted ophthalmic surgery.

BACKGROUND OF THE INVENTION

With significant developments in laser technology and its application to ophthalmology, laser surgery has become the technique of choice for ophthalmic procedures, such as refractive surgery for correcting myopia, hyperopia, astigmatism, and so on, and cataract surgery for treating and/or removing a cataractic lens. Laser eye surgery generally uses different types of laser beams, such as ultraviolet lasers, infrared lasers, and near infrared, ultra-short pulsed lasers, for various procedures and indications.

A surgical laser beam is preferred over manual tools like microkeratomes because it can be focused precisely on extremely small amounts of ocular tissue, thereby enhancing accuracy and reliability. For example, in the commonly-known LASIK (Laser Assisted In Situ Keratomileusis) procedure, an ultra-short pulsed laser is used to cut a corneal flap to expose the corneal stroma for photoablation with an excimer laser. Ultra-short pulsed lasers emit radiation with pulse durations as short as 10 femtoseconds and as long as 3 nanoseconds, and a wavelength between 300 nm and 3000 nm. Besides cutting corneal flaps, ultra-short pulsed lasers are used to perform cataract-related surgical procedures, including capsulorhexis, capsulotomy, as well as softening and/or breaking of the cataractous lens. Examples of laser systems that provide ultra-short pulsed laser beams include the Abbott Medical Optics iFS™ Advanced Femtosecond Laser and the IntraLase™ FS Laser.

Conventional ophthalmic surgical laser systems generally include an operator interface used by the system operator to set-up, control, monitor, and direct the laser treatment. For obvious reasons, the laser beam's ability to accurately and precisely incise tissue, as well as its ability to properly determine the incision depth, —(e.g., depth measured from the surface of the cornea, the laser system interface, and/or the laser source)—, are important.

As such, eye biometry information is often taken before surgery to measure the location, depth, and length of all planes of a patient's eye. A system for obtaining ophthalmic biometry data is described in U.S. Pat. No. 7,887,184, issued to Baer et al., which is incorporated here by reference in its entirety. Pre-surgical measurements, however, may not account for how the internal geometry of the eye is affected by an ophthalmic patient interface, which is typically used to restrain eye movement during surgery. Examples of ophthalmic patient interface devices used to stabilize the eye are described in commonly-owned U.S. Pat. No. 6,863,667, issued to Webb et al., U.S. Pat. No. D462,442 issued to Webb, U.S. Pat. No. 6,623,476, issued to Juhasz et al., and co-pending U.S. patent application Ser. No. 13/230,590, which are incorporated here by reference. Furthermore, most pre-surgical measurements generally require a separate or additional device from the surgical system, adding cost. For example, some surgical systems add additional pre-surgery imaging devices, such as an optical coherence tomographer (OCT). Besides adding system costs, additional imaging devices like OCT require regular calibration and maintenance to maintain strong a spatial correlation between the surgical laser and the OCT.

Accordingly, there is a need for improved systems and methods for depth detection during laser ophthalmic surgery.

SUMMARY OF THE INVENTION

Embodiments of this invention generally relate to ophthalmic laser procedures and, more particularly, to systems and methods for automatic depth (or Z) detection before, during, or after laser-assisted ophthalmic surgery. During an ophthalmic laser procedure, the operator (or surgeon) needs to make accurate and precise incisions using the laser beam. With the automatic depth detection systems and methods, the same laser that makes the surgical incisions also measures the tissue depth for where the incisions should occur. In one embodiment, an ophthalmic surgical laser system may include a laser delivery system to deliver a pulsed laser beam to photoalter an eye, a mirror to transmit a portion of the reflected light of the pulsed laser beam, a lens positioned to focus the portion of reflected light onto a detector, such as for example, a charge-coupled device (CCD), and a depth encoder configured to detect treatment depth of the pulsed laser beam according to one or more of color, intensity, or shape of the focused spot on the detector.

This summary and the following detailed description are merely exemplary, illustrative, and explanatory, and are not intended to limit, but to provide further explanation of the invention as claimed. Additional features and advantages of the invention will be set forth in the descriptions that follow, and in part will be apparent from the description, or may be learned by practice of the invention. The objectives and other advantages of the invention will be realized and attained by the structure particularly pointed out in the written description, claims and the appended drawings.

BRIEF DESCRIPTION OF THE DRAWINGS

Understanding this invention will be facilitated by the following detailed description of the preferred embodiments considered in conjunction with the accompanying drawings, in which like numerals refer to like parts throughout the different views. Like parts, however, do not always have like reference numerals. Further, the drawings are not drawn to scale, and emphasis has instead been placed on illustrating the principles of the invention. All illustrations are intended to convey concepts, where relative sizes, shapes, and other detailed attributes may be illustrated schematically rather than depicted literally or precisely.

DETAILED DESCRIPTION OF THE PREFERRED EMBODIMENTS

Figure 1:
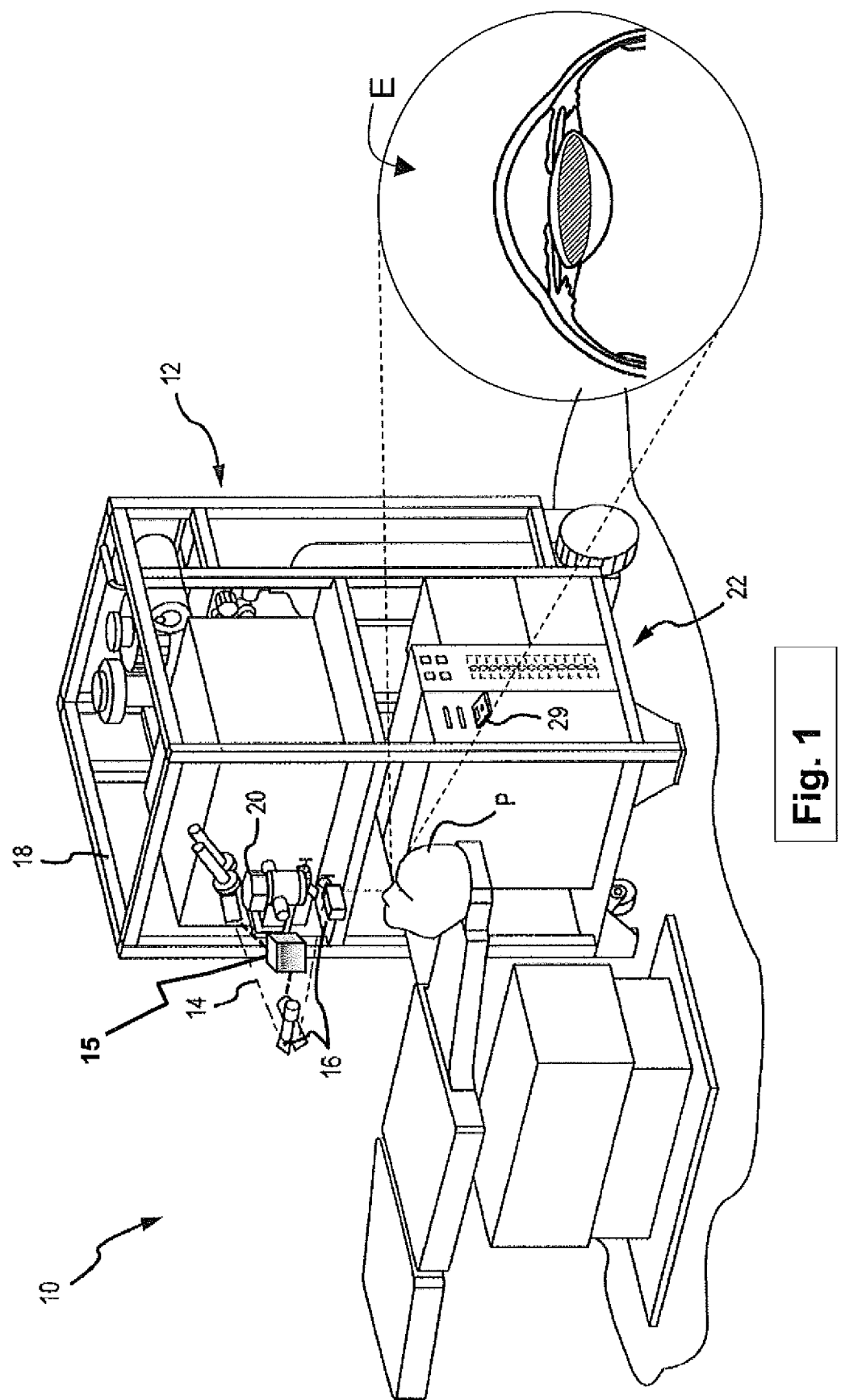
FIG. 1 is a perspective view of a surgical ophthalmic laser system according to an embodiment of the present invention.

Embodiments of this invention are generally directed to systems and methods for ophthalmic laser surgery, and more particularly to systems and methods for depth (or Z) detection before, during, or after laser-assisted ophthalmic surgery. In one embodiment, the same laser used for the surgical operation is also utilized for the depth measurement for the surgical incision before, during, or after the surgery.

According to an embodiment, the depth (or Z) position of a patient's ocular lens capsule is detected during a laser cataract surgery ("femtophaco") procedure performed with a surgical laser system, such as for example, the Abbott Medical Optics iFS™ Advanced Femtosecond Laser or IntraLase™ FS Laser, as well as other systems in the market providing ultra-short pulsed laser beams for laser-assisted cataract surgery. The plasma light of the ultra-short pulsed laser delivered at a focal point within the patient's eye is collected and collimated by the surgical laser system's objective lens and telescope. About ten percent of this collected plasma light passes through a 45 degree mirror and is focused by an L2 lens onto an imaging camera or detector, for example, a charge-coupled device (CCD). The color, shape, and intensity of the image or spot on the CCD will be different for plasma light generated and collected from within the aqueous humor, the capsule, or the lens. Further, using a Z (or depth) encoder known in the art (see, e.g., U.S. application Ser. No. 12/275,518, filed Nov. 21, 2008, entitled, "Apparatus, System, and Method for Precision Depth Measurement," which is incorporated here by reference in its entirety), the data captured by the CCD can be used to determine the depth in microns, which can be used for the incision. Generally, when the CCD is in the focal plane of the L2 lens, the spot on the CCD does not move during x/y scanning primarily because of the placement of the L2 lens and the detector before a laser beam steering apparatus, such as Galvo-driven mirrors.

According to an embodiment, to detect the lens capsule in a capsulorhexis operation, as is performed during cataract surgery, the surgical laser system is first programmed for a predetermined vertical side cut with a diameter of, for example, about 5-6 mm. The surgical laser system directs the vertical side cut to move down to the direction of the lens capsule. The starting depth is typically about 3 mm. As such, the programmed depth typically extends from about 3 mm to about 4 mm. This is the depth range where the anterior lens capsule surface is most likely to be located. When the plasma light generated by the laser is from within the aqueous humor, the intensity of the spot on the CCD will be low. When the laser beam first reaches the lens capsule, there will be a sudden increase in spot intensity. If the patient's ocular lens is tilted with respect to the optical axis of the objective lens, or is otherwise de-centered, the spot intensity will pulsate as the plasma is generated either in the aqueous humor, in the lens capsule, or in the lens. When the laser proceeds deeper into the ocular tissue and is entirely within the lens, the captured plasma light intensity detected via the CCD is nearly constant over each side cut revolution. A constant intensity of the spot indicates that capsulorhexis has been completed.

According to another embodiment, the ability to monitor what tissue is undergoing laser treatment, and consequently where the laser surgery is taking place, enables one to reduce the treatment process time through use of variable depth incrementations. For example, the vertical depth may be incremented in steps (or layered separations) of 10 µm. When the first plasma signal appears on the CCD and has a predetermined intensity, the layer separation is changed to 2 µm. The incision continues with 2 µm layer separation until the capsulorhexis is completed.

According to an embodiment, the surgical laser system is programmed to perform a side cut pattern that is repeated over depth so as to detect the cornea while performing a penetrating corneal incision. The side cut pattern can start from above the anterior surface of the cornea or below the posterior cornea, in the anterior chamber. In this case, the plasma light generated by the laser in glass (as found in a cone-lens of a patient interface device), cornea, or aqueous humor will produce a spot with differing color, shape, or intensity on a detector, such as a CCD. Hence, by monitoring the spot characteristics on the CCD, the depth encoder, as well as the beam steering for direction, one can determine where the laser is currently firing, and can decide whether to proceed with the treatment, or to stop.

According to an embodiment, when the laser beam is focused onto an optical interface, the back-reflected beam is also focused onto the CCD. The spot size on the CCD will be about 30 µm (when using a 100 mm focal length L2 lens). When the laser beam is focused above or below the interface by about 10 µm, the spot size on the CCD will be about 60 µm. Using the spot size variance, the system can measure the depth with an accuracy of about 3-5 µm. This automatic depth (or auto-z) measurement can thus be used to compensate for any optical interface position variation, which may shift the zero depth reference of a laser surgical system. It is noted that this auto-z technique does not require laser beam intensities which may cause optical damage to the optical interface cone glass.

When the laser beam is focused on any of the interfaces (for example, patient interface lens-cone-glass/air, patient interface lens-cone-glass/cornea, cornea/aqueous humor, aqueous humor/capsule, and the like), a spot with sharp intensity will appear on the CCD. Taking into account the reflectivity of the different interfaces (for example, 3.4% for patient interface lens-cone-glass/air, 0.61% for patient interface lens-cone glass/cornea, 0.034% for cornea/aqueous humor, and 0.19% for aqueous humor/capsule), the depth and spatial relation of the various interfaces can be measured without causing optical damage. The depth data can be displayed graphically, or in three-dimensional renderings to assist treatment planning.

According to an embodiment, the spot on the CCD may further be used as an onboard automated laser spot size/quality monitor, thus replacing the external spot size camera used in the surgical laser system.

According to an embodiment, one can integrate the onboard laser spot size/quality monitor as feedback into an adaptive optics configuration. Deformable mirrors, or any wavefront altering device, in the laser delivery path provides the main mechanism for compensating optical aberration, thereby tightly focusing the laser spot. A mapping of optical aberration over the surgical volume (plane and depth) may be used to guide aberration management. The effectiveness of aberration management is confirmed via the spot quality imaged by the CCD. Note that this aberration management can be performed either prior to, or during laser treatment.

According to an embodiment, a program code, algorithm, or software periodically or continuously monitors information received from the eye E on the CCD. This monitoring may or may not be based on real-time data acquisition and processing. The depth position may be dynamically detected based on this information.

FIG. 1 illustrates a surgical laser system 10 according to an embodiment. The surgical laser system 10 includes a laser 12 that produces a laser beam 14 which generates laser beam pulses. Laser 12 is optically coupled to laser delivery optics 16, which, under the direction of a computer system 22, directs laser beam 14 to an eye E of patient P. A delivery optics support structure (not shown here for clarity) extends from a frame 18 supporting laser 12. A microscope 20 is mounted on the delivery optics support structure. A visual fixation system 15 is generally coupled to laser 12, laser delivery optics 16 and the delivery optics support structure. The visual fixation system 15 may also operate under the direction of computer system 22. Laser 12 may be designed to provide a feedback stabilized fluence at the patient's eye, delivered via delivery optics 16.

U.S. Pat. No. 7,351,241 describes methods of photoalteration, and is incorporated here by reference. Other devices or systems may also be used to generate pulsed laser beam 14. For example, non-ultraviolet (UV), ultra-short pulsed laser technology can produce pulsed laser beam 14 having pulse durations measured in the femtoseconds and picoseconds range. Some of the non-UV, ultra-short pulsed laser technology may be used in ophthalmic applications. For example, U.S. Pat. No. 5,993,438, incorporated here by reference, discloses a device for performing ophthalmic surgical procedures to effect high-accuracy corrections of optical aberrations, as well as an intrastromal photodisruption technique for reshaping the cornea using a non-UV, ultra-short (e.g., femtosecond pulse duration), pulsed laser beam that propagates through corneal tissue and is focused at a point below the surface of the cornea to photodisrupt stromal tissue at the focal point.

Although the laser system 10 may be used to photoalter a variety of materials (e.g., organic, inorganic, or a combination thereof), the laser system 10 is suitable for ophthalmic applications in one embodiment. In this case, the focusing optics direct the pulsed laser beam 14 toward an eye E (for example, onto or into a cornea) for plasma mediated (for example, non-UV) photoablation of superficial tissue, or into the stroma of the cornea for intrastromal photodisruption of tissue. In this embodiment, the surgical laser system 10 may also include a lens to change the shape (for example, flatten or curve) of the cornea prior to scanning the pulsed laser beam 14 toward the eye E. The laser system 10 is capable of generating the pulsed laser beam 14 with physical characteristics similar to those of the laser beams generated by a laser system disclosed in U.S. Pat. Nos. 4,764,930 and 5,993,438, which are incorporated here by reference.

For example, the ophthalmic laser system 10 can produce an ultra-short pulsed laser beam 14 for use as an incising laser beam 14. This pulsed laser beam 14 preferably has laser pulses with durations as long as a few nanoseconds or as short as a few femtoseconds. For intrastromal photodisruption of the tissue, the pulsed laser beam 14 has a wavelength that permits the pulsed laser beam 14 to pass through the cornea without absorption by the corneal tissue. The wavelength of the pulsed laser beam 14 is generally in the range of about 3 µm to about 1.9 nm, preferably between about 400 nm to about 3000 nm, and the irradiance of the pulsed laser beam 14 for accomplishing photodisruption of stromal tissues at the focal point is typically greater than the threshold for optical breakdown of the tissue. Although a non-UV, ultra-short pulsed laser beam is described in this embodiment, the pulsed laser beam may have other pulse durations and different wavelengths in other embodiments.

Computer system 22 may comprise (or interface with) a conventional or special computer, for example, PC, laptop, workstation, embedded real-time operating system/processor, field programmable gate array (FPGA), and so on, including the standard user interface devices such as a keyboard, a mouse, a touch pad, foot pedals, a joystick, a touch screen, an audio input, a display monitor, and the like. Computer system 22 typically includes an input device such as a magnetic or optical disk drive, or an input interface such as a USB connection, a wired and/or wireless network connection, or the like. Such input devices or interfaces are often used to download a computer executable code to a storage media 29, and may embody any of the methods of the present invention. Storage media 29 may take the form of an optical disk, a data tape, a volatile or non-volatile memory, RAM, or the like, and the computer system 22 includes the memory and other standard components of modern computer systems for storing and executing this code. Storage media 29 includes one or more fixation maps, and may optionally include a treatment map, and/or an ablation table. Storage media 29 may alternatively be remotely operatively coupled with computer system 22 via network connections such as LAN, the Internet, or via wireless methods such as WLAN, Bluetooth, or the like.

Additional components and subsystems may be included with laser system 10, as should be understood by those of skill in the art. For example, spatial and/or temporal integrators may be included to control the distribution of energy within the laser beam, as described in U.S. Pat. No. 5,646,791, which is incorporate here by reference. Ablation effluent evacuators/filters, aspirators, and other ancillary components of the surgical laser system are known in the art. Further details of suitable systems for performing a laser ablation procedure can be found in commonly assigned U.S. Pat. Nos. 4,665,913, 4,669,466, 4,732,148, 4,770,172, 4,773,414, 5,207,668, 5,108,388, 5,219,343, 5,646,791 and 5,163,934, which are incorporated here by reference.

Figure 2:
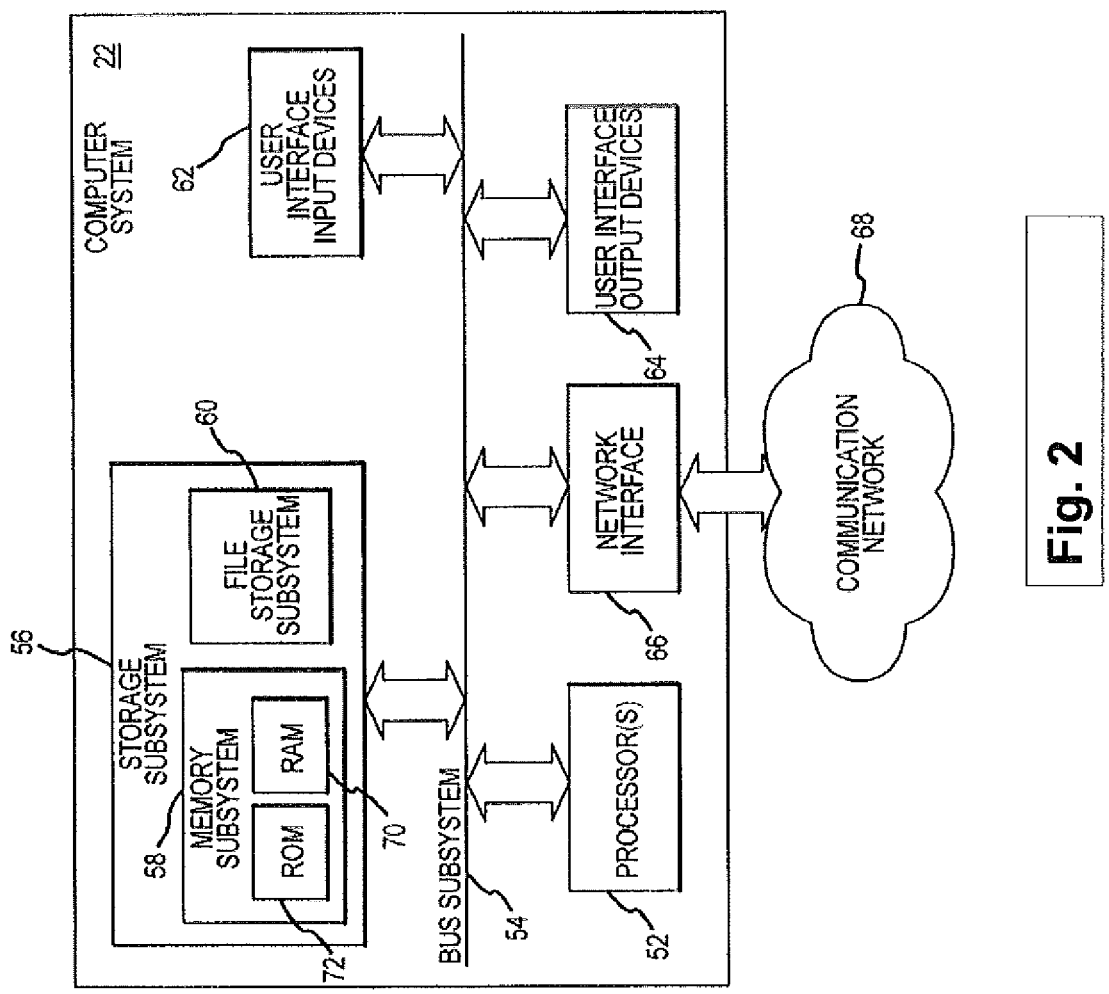
FIG. 2 is a simplified diagram of a computer system according to an embodiment of the present invention.

FIG. 2 illustrates a simplified block diagram of an exemplary computer system 22 that may be used by the laser surgical system 10 according to an embodiment of this invention. Computer system 22 typically includes at least one processor 52 which may communicate with a number of peripheral devices via a bus subsystem 54. These peripheral devices may include a storage subsystem 56, comprising a memory subsystem 58 and a file storage subsystem 60 (which may include storage media 29), user interface input devices 62, user interface output devices 64, and a network interface subsystem 66. Network interface subsystem 66 provides an interface to outside networks 68 and/or other devices.

User interface input devices 62 may include a keyboard, pointing devices such as a mouse, trackball, touch pad, or graphics tablet, a scanner, foot pedals, a joystick, a touch screen incorporated into the display, audio input devices such as voice recognition systems, microphones, and other types of input devices. User interface input devices 62 are often used to download a computer executable code from a storage media 29 embodying any of the methods of the present invention. User interface input devices 62 are also used to control an eye fixation system. In general, the term "input device" is intended to include a variety of conventional and proprietary devices and ways to input information into computer system 22.

User interface output devices 64 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, the term "output device" is intended to include a variety of conventional and proprietary devices and ways to output information from computer system 22 to a user.

Storage subsystem 56 can store the basic programming and data constructs that provide the functionality of the various embodiments of the present invention. For example, a database and modules implementing the functionality of the methods of the present invention, as described herein, may be stored in storage subsystem 56. These software modules are generally executed by processor 52. In a distributed environment, the software modules may be stored on a plurality of computer systems and executed by processors of the plurality of computer systems. Storage subsystem 56 typically comprises memory subsystem 58 and file storage subsystem 60.

Memory subsystem 58 typically includes a number of memories including a main random access memory (RAM) 70 for storage of instructions and data during program execution and a read only memory (ROM) 72 in which fixed instructions are stored. File storage subsystem 60 provides persistent (non-volatile) storage for program and data files, and may include storage media 29 (FIG. 1). File storage subsystem 60 may include a hard disk drive along with associated removable media, a Compact Disk (CD) drive, an optical drive, DVD, solid-state removable memory, and/or other removable media cartridges or disks. One or more of the drives may be located at remote locations on other connected computers at other sites coupled to computer system 22. The modules implementing the functionality of the present invention may be stored by file storage subsystem 60.

Bus subsystem 54 provides a mechanism for letting the various components and subsystems of computer system 22 communicate with each other as intended. The various subsystems and components of computer system 22 need not be at the same physical location but may be distributed at various locations within a distributed network. Although bus subsystem 54 is shown schematically as a single bus, alternate embodiments of the bus subsystem may utilize multiple busses.

Computer system 22 itself can be of varying types including a personal computer, a portable computer, a workstation, a computer terminal, a network computer, a control system in a wavefront measurement system or laser surgical system, a mainframe, or any other data processing system. Due to the ever-changing nature of computers and networks, the description of computer system 22 depicted in FIG. 2 is intended only as an example for purposes of illustrating one embodiment of the present invention. Many other configurations of computer system 22, having more or fewer components than those depicted in FIG. 2, are possible.

Figure 3:
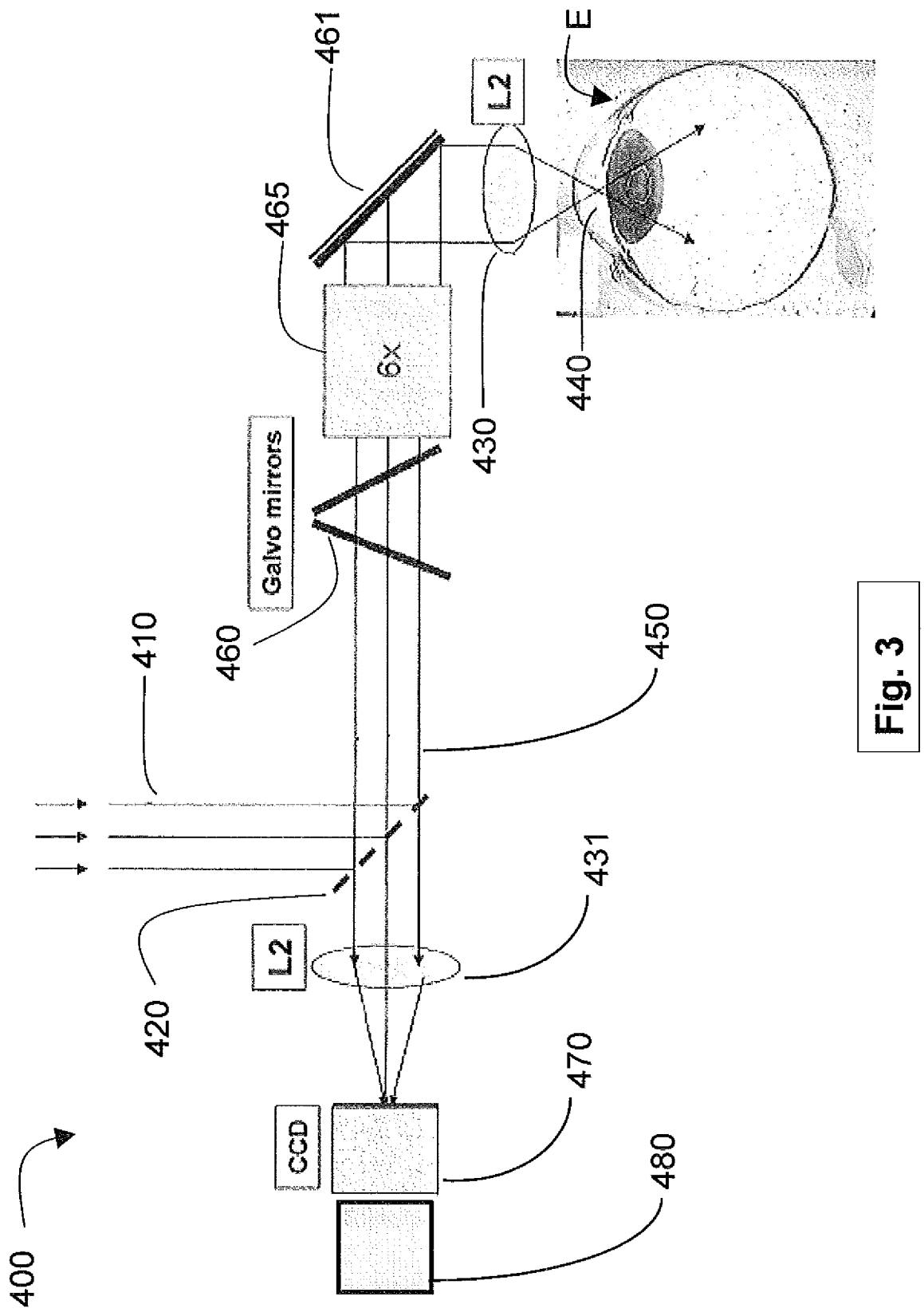
FIG. 3 is an illustration of a light path in a surgical ophthalmic laser system according to an embodiment of the present invention.

FIG. 3 shows an exemplary implementation 400 in laser surgical system 10 to enable automatic depth detection. In general, the optics delivery system includes, among other components, semitransparent mirror 420 with 10% transmission (e.g., R=90, T=10%), Galvo mirrors 460, a 6× telescope 465, and an objective L2 lens 430. The laser beam 410 is directed to an eye E. The laser produces plasma light 440 in the focal point of the laser beam in the eye E. The plasma light is collected and collimated by the objective lens 430. Ten percent of the backward propagating plasma light 450 is transmitted by mirror 420 and is focused by 2 lens 431 onto the CCD 470. The Z-encoder 480, coupled to the CCD 470, uses data from the CCD 470 to generate the depths for the aqueous humor, the capsule, and the lens of the eye E. The data on the CCD includes, for example, the color, shape, and intensity of the spot on the CCD 470.

In alternative embodiments, mirror 420 may have a less than 10%, for example, as low as 1%, transmission rate. Further, a sensitive photodiode, photodiode array, quadrant detector (not shown), or a CMOS imaging sensor may be used in place of the CCD 470. Photodiodes are typically faster, more sensitive, and less expensive. Similarly, CMOS sensors are generally faster and may cost less than other detectors. More than one mirror may also be positioned between the L2 lens 431 and the first Galvo mirror 460. A beam-splitter may be used to separate out light for the CCD 470. It may also be used to enable both an imaging sensor and a photodiode configuration.

Figure 4:
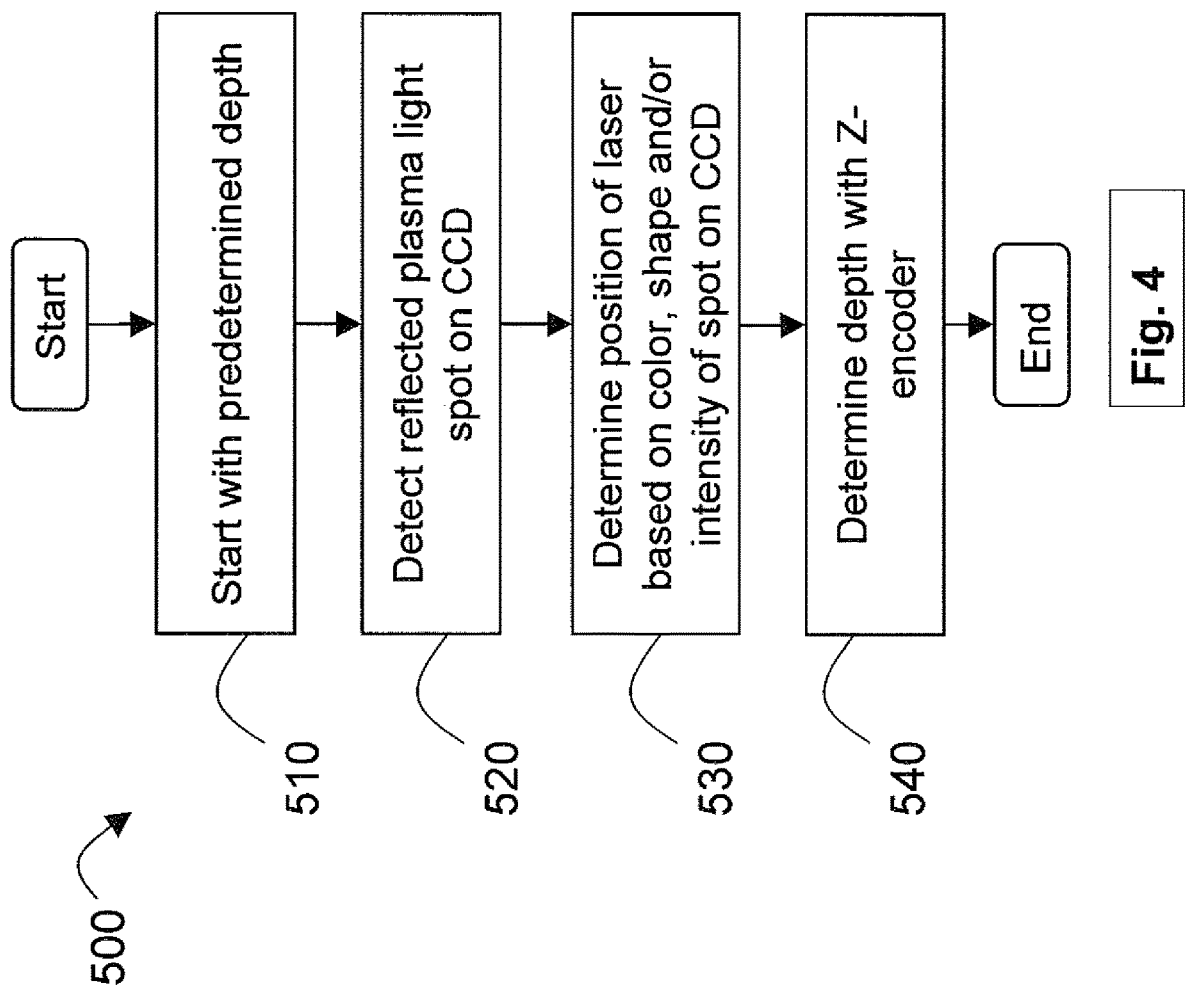
FIG. 4 is a flowchart illustrating a process according to an embodiment of the present invention.

FIG. 4 illustrates a process 500 of the laser system 10 according to an embodiment. The laser surgical system 10 starts the surgical procedure with a predetermined depth (Action Block 510). When the laser beam is focused on a target in the patient's eye, at least a portion of the plasma light is detected on CCD 470 (Action Block 520). Based on at least one of the color, shape, and intensity of the focused spot on the CCD 470, the laser system 10 determines whether the target (the focal point of the laser beam in the eye E) is the aqueous humor, the capsule, or the lens (Action Block 530). The data from the CCD is also used by the Z-encoder to determine the depth for the target (Action Block 540).

Although this invention has been described and pictured in an exemplary form with a certain degree of particularity, and describes the best mode contemplated of carrying out the invention, and of the manner and process of making and using it, those skilled in the art will understand that various modifications, alternative constructions, changes, and variations can be made in the device and method without departing from the spirit or scope of the invention. Thus, it is intended that this invention cover all modifications, alternative constructions, variations, and combination and arrangement of parts and steps that come within the spirit and scope of the invention as generally expressed by the following claims and their equivalents.

What is claimed is:

1. An ophthalmic surgical laser system for a capsulorhexis operation, comprising:
   a laser delivery system for delivering a pulsed laser beam to a subject's eye to perform capsulorhexis, the pulsed laser beam having ultra-short pulses in a femtoseconds and picoseconds range, the laser delivery system being configured to deliver the pulsed laser beam to the eye according to a vertical side cut pattern which is a cut pattern that forms a circular revolution located at a depth, and to move the vertical side cut pattern in the depth direction from an aqueous humor toward and into a lens capsule and a lens in the lens capsule;
   a mirror positioned to transmit at least a portion of collected plasma light from the eye, the plasma light being generated in the eye by the pulsed laser beam when it photoalters tissues of the eye by plasma mediated photoablation which generates a plasma;
   a lens positioned to focus the transmitted collected plasma light onto a detector to form spots on the detector;
   a Z-position encoder operatively coupled to the detector; and
   a computer comprising a non-volatile memory storing computer-executable code and a processor configured to execute the computer-executable code, wherein the processor is configured to control the Z-position encoder to determine a current location of photoablation in the subject's eye based on data captured by the detector which indicates the spots formed by the collected plasma light focused on the detector, including determining whether the current location of photoablation is within the aqueous humor or has reached the lens capsule based on detecting an increase in intensity of the spots formed by the plasma light, and determining whether the current location of photoablation defined by the vertical side cut pattern is partially or entirely within the lens based on whether the intensity of the spots formed by the plasma light is pulsating or is constant over each side cut revolution of the vertical side cut pattern.

2. The system of claim 1, wherein the detector is a charge-coupled device (CCD).

3. The system of claim 1, wherein the detector is a photodiode.

4. The system of claim 1, wherein the detector is a quadrant detector.

5. The system of claim 1, wherein the mirror has a 10% or less transmission rate.

6. The system of claim 1, wherein each spot formed by the collected plasma light focused on the detector further includes at least one of color and shape.

7. A method of performing capsulorhexis operation and automatically
   detecting a depth measurement using an ophthalmic laser-based treatment system having a mirror, a lens, a detector, a non-volatile memory storing computer-executable code, and a process configured to execute the computer-executable code, the method comprising the steps of:
   delivering a pulsed laser beam to a subject's eye according to a vertical side cut pattern which is a cut pattern that forms a circular revolution located at a depth, and moving the vertical side cut pattern in the depth direction from an aqueous humor toward and into a lens capsule and a lens in the lens capsule to perform capsulorhexis, the pulsed laser beam having ultra-short pulses in a femtoseconds and picoseconds range;
   transmitting by the mirror at least a portion of collected plasma light from the eye, the plasma light being generated in the eye by the pulsed laser beam when it photoalters eye tissues by plasma mediated photoablation which generates a plasma;
   focusing the collected plasma light by the lens on to the detector to form spots on the detector; and
   the processor controlling a Z-position encoder to determine a current location of photoablation in the subject's eye based on data captured by the detector which indicates the spots formed by the collected plasma light focused on the detector, including determining whether the current location of photoablation is within the aqueous humor or has reached the lens capsule based on detecting an increase in intensity of the spots formed by the plasma light, and determining whether the current location of photoablation defined by the vertical side cut pattern is partially or entirely within the lens based on whether the intensity of the spots formed by the plasma light is pulsating or is constant over each side cut revolution of the vertical side cut pattern.

8. The method of claim 7, further comprising determining at least one of color and shape of the spots formed by the reflected light focused on the detector.

* * * * *